(12) United States Patent
Zhang et al.

(10) Patent No.: US 11,317,610 B2
(45) Date of Patent: May 3, 2022

(54) **METHOD OF CONSTRUCTING ZEBRAFISH *NOTCH1A* MUTANTS**

(71) Applicant: Shanghai Ocean University, Shanghai (CN)

(72) Inventors: Qinghua Zhang, Shanghai (CN); Ce Ji, Shanghai (CN)

(73) Assignee: Shanghai Ocean University, Shanghai (CN)

( * ) Notice: Subject to any disclaimer, the term of this patent is extended or adjusted under 35 U.S.C. 154(b) by 249 days.

(21) Appl. No.: 16/422,975

(22) Filed: May 25, 2019

(65) Prior Publication Data

US 2019/0357507 A1  Nov. 28, 2019

(30) Foreign Application Priority Data

May 28, 2018 (CN) .......................... 201810527941.9

(51) Int. Cl.
| | | |
|---|---|---|
| *C12N 15/00* | (2006.01) | |
| *A01K 67/027* | (2006.01) | |
| *C07K 14/48* | (2006.01) | |
| *C12N 15/873* | (2010.01) | |
| *C12N 15/90* | (2006.01) | |
| *A61K 38/17* | (2006.01) | |

(52) U.S. Cl.
CPC .......... *A01K 67/0276* (2013.01); *C07K 14/48* (2013.01); *C12N 15/873* (2013.01); *C12N 15/902* (2013.01); *A01K 2207/15* (2013.01); *A01K 2217/05* (2013.01); *A01K 2217/075* (2013.01); *A01K 2227/40* (2013.01); *A61K 38/1706* (2013.01); *C12N 2310/20* (2017.05)

(58) Field of Classification Search
CPC ........................ A01K 67/0276; A01K 2227/40
USPC .......................................................... 800/20
See application file for complete search history.

(56) References Cited

FOREIGN PATENT DOCUMENTS

| CN | 105985982 A | 10/2016 |
|---|---|---|
| CN | 109679953 A | 4/2019 |

OTHER PUBLICATIONS

Ablain (Developmental Cell, 2015, vol. 32, No. 6, p. 756-764).*
GenBank X69088.1 (Zebrafish notch1a gene) available 1993.*
Xuehong Dong, "A Preliminary Study on the Role of Notch Molecules Induced by Vibrio parahaemolyticus in Innate Immune Responses" China Excellent Doctoral Dissertation Full-text Database (Master) Agricultural Science Series, Issue 02, pp. D052-D195.
Nannan Chang et al. "Genome editing with RNA-guided Cas9 nuclease in zebrafish embryos", cell research, vol. 23, pp. 465-472.
D.E.Lancefield, "Linkage Relations of the Sex-Linked Characters in *Drosophila* Obscurai", Genetics, vol. 7, pp. 335-384.
W.J.Welshons, "Genetic basis for two types of recessive lethality at the notch locus of *Drosophila*", Genetics, vol. 68, pp. 259-268.

* cited by examiner

*Primary Examiner* — Michael C Wilson

(57) ABSTRACT

A method of constructing a zebrafish notch1a mutant using CRISPR/Cas9 technique. The method includes: determining a target for knocking out notch1a; using primers T7-notch1a-sfd and tracr rev for PCR amplification with a pUC19-gRNA scaffold plasmid as a template; transcribing PCR product in vitro followed by purification to obtain gRNA; and microinjecting the gRNA and a Cas9 mRNA into a zebrafish embryo followed by culture to obtain an notch1a mutant of stable inheritance. The invention selects a specific target and utilizes CRISPR/Cas9 technique to knock out the notch1a in the zebrafish without destroying other genes, generating the zebrafish notch1a mutant. Moreover, the invention also discloses the phenotype of the zebrafish notch1a mutant, which plays a significant role in studying the effect of the Notch1a receptor in the Notch signaling pathway.

8 Claims, 5 Drawing Sheets

Specification includes a Sequence Listing.

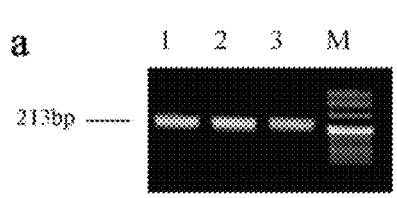 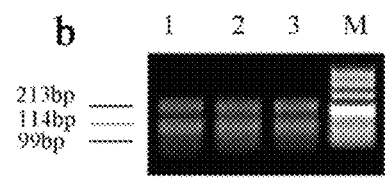
FIG. 1a          FIG. 1b
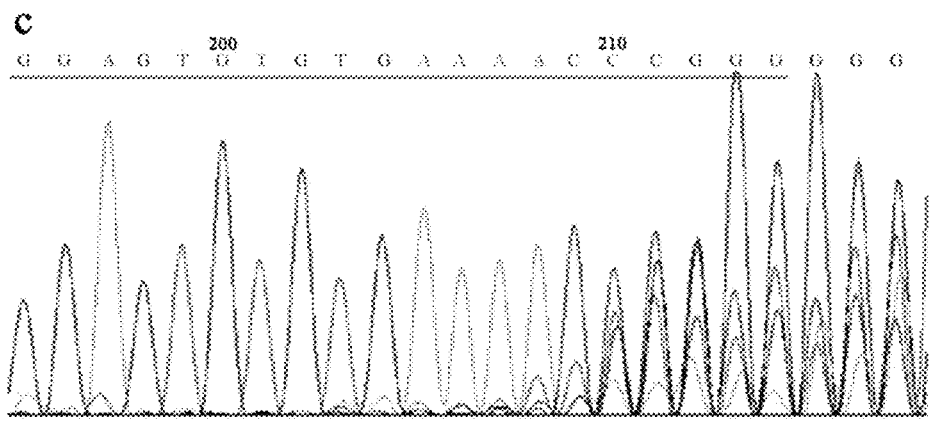
FIG. 1c

SEQUENCE LISTING

<160> NUMBER OF SEQ ID NOS: 5

<210> SEQ ID NO 1
<211> LENGTH: 20
<212> TYPE: DNA
<213> ORGANISM: Artificial Sequence
<220> FEATURE:
<223> OTHER INFORMATION: synthetic

<400> SEQUENCE: 1
ggagtgtgtg aaaacctgcg                                        20

<210> SEQ ID NO 2
<211> LENGTH: 57
<212> TYPE: DNA
<213> ORGANISM: Artificial Sequence
<220> FEATURE:

```
<223> OTHER INFORMATION: synthetic

<400> SEQUENCE: 2
taatacgact cactatagga gtgtgtgaaa acctgcggtt ttagagctag aaatagc        57

<210> SEQ ID NO 3
<211> LENGTH: 25
<212> TYPE: DNA
<213> ORGANISM: Artificial Sequence
<220> FEATURE:
<223> OTHER INFORMATION: synthetic

<400> SEQUENCE: 3
aaaaaaagca ccgactcggt gccac                                          25

<210> SEQ ID NO 4
<211> LENGTH: 18
<212> TYPE: DNA
<213> ORGANISM: Artificial Sequence
<220> FEATURE:
<223> OTHER INFORMATION: synthetic

<400> SEQUENCE: 4
cgtgtgaggt ggacatta                                                  18

<210> SEQ ID NO 5
<211> LENGTH: 22
<212> TYPE: DNA
<213> ORGANISM: Artificial Sequence
<220> FEATURE:
<223> OTHER INFORMATION: synthetic

<400> SEQUENCE: 5
cattagttaa gtgaggtgtg ag                                             22
```

METHOD OF CONSTRUCTING ZEBRAFISH *NOTCH1A* MUTANTS

REFERENCE TO AN ELECTRONIC SEQUENCE LISTING

The contents of the electronic sequence listing (Untitled_ST25.txt; Size: 2,000 bytes; and Date of Creation: Jul. 22, 2019) is herein incorporated by reference in its entirety.

CROSS-REFERENCE TO RELATED APPLICATIONS

This application claims the benefit of priority from Chinese Patent Application No. 201810527941.9, filed on May 28, 2018. The content of the aforementioned application, including any intervening amendments thereto, is incorporated herein with reference in its entirety.

TECHNICAL FIELD

The present disclosure relates to zebrafish mutants, and more specifically to a method of preparing zebrafish notch1a mutants using CRISPR/Cas9 technique and determination of phenotypes of the mutants.

BACKGROUND OF THE INVENTION

The Notch signaling pathway is thought to play an important role in early development and in the functioning of various cells. It is mainly involved in cell proliferation and differentiation, and regeneration of stem cells. Notch receptors are highly conserved, so that their function is dependent on the presence of specific ligands on adjacent cells. In addition, the Notch signaling pathway also plays an important role in the development of the body, the formation and proliferation of tumor cells, and the regulation of genetic diseases. In the nervous system, the Notch signaling pathway also has various regulatory effects, affecting the differentiation and quantity of neural stem cells and regulating the formation of a variety of cells.

CRISPR/Cas (Clustered Regularly Interspersed Short Palindromic Repeats, CRISPR/CRISPR-associated genes, Cas gene) system is an acquired immune system in microorganisms that uses a guide RNA nuclease to cleave foreign genes. There are three types of CRISPR/Cas including type I, type II and type III, where type II requires only one Cas9 endonuclease to cleave DNA duplex, so that the type II is a CRISPR/Cas9 system. The system consists of a Cas9 nuclease and two non-coding RNAs: CRISPR RNA (crRNA) and trans-activating crRNA. Compared to other gene editing technologies, such as ZFNs and TALENs, the CRISPR/Cas9 system has advantages of easy synthesis, high targeting efficiency and simultaneous editing of multiple genes. The high efficiency of the CRISPR/Cas9 system can not only ensure the occurrence of gene mutations in somatic cells, but also can cause mutations in germ cells, such that the mutated genes can be passed to the next generation. Because of the efficient destruction of the system for the gene reading frame sequence and the rapid growth of zebrafish, of it is feasible to establish a stably heritable zebrafish mutant strain in a short time, facilitating the further investigations on gene function.

It is found that the Notch1a in zebrafish is highly similar to the NOTCH1 in mammals. The knockout mutants can be effectively used to investigate the related functions of the Notch pathway. Currently, the Notch1 mutation in mice is less explored, and it costs too much to construct and maintain a mouse model. Furthermore, the knocking down of notch1a in zebrafish by morpholino fails to generate a phenotype of disorders of somites and intersegmental blood vessels.

The zebrafish notch1a gene is located on chromosome 21 and has three transcripts. The longest transcript mRNA has a length of 7474 bp, encodes 2438 amino acids and contains 33 exons and 32 introns. Therefore, there is great difficulty in selecting a functional target of which the knockout may result in function loss of the entire gene and appearance of easy-to-screen phenotype, which is like looking for a needle in a haystack. A desirable targeting site is critical to the preparation of the mutant. In addition, it is of great significance to successfully construct a notch1a mutant and use this mutant as a model to study the function of the Notch pathway in early development.

SUMMARY OF THE INVENTION

The invention aims to provide a method of constructing a zebrafish notch1a mutant using CRISPR/Cas9 technique and the determination of a phenotype of the mutant. The invention selects a specific targeting site on the 16th exon and uses the CRISPR/Cas9 technique to construct a notch1a mutant. A total of four mutation types are generated due to the randomness, consisting of 4 bp, 10 bp, 19 bp and 31 bp deletions in the vicinity of the target. Early termination is observed when such mutated sequences are used as templates for the amino acid translation. Specifically, the translation termination respectively occurs at the amino acid residue 947 in the 4 bp-deletion mutant, at the amino acid residue 945 in the 10 bp-deletion mutant, at the amino acid residue 942 in the 19 bp-deletion mutant and at the amino acid residue 938 in the 31 bp-deletion mutant. The mutant was observed to have a phenotype involving disorders of somites and intersegmental blood vessels, and these four different mutants have consistent phenotypic characteristics.

The technical solutions of the invention are described below.

The invention discloses a method of preparing a zebrafish notch1a mutant, comprising:
(1) determining a target for knocking out notch1a on the 16th exon of a sequence of the zebrafish notch1a gene;
(2) designing a primer for amplification according to a sequence of the target determined in step 1;
(3) using primers T7-notch1a-sfd and tracr rev for PCR amplification with a pUC19-gRNA scaffold plasmid as a template;
(4) transcribing PCR product obtained in step 3 in vitro followed by purification to obtain gRNA;
(5) using a pXT7-hCas9 plasmid as a template to synthesize Cas9 mRNA by in vitro transcription;
(6) microinjecting the gRNA and the Cas9 mRNA into a one-cell stage zebrafish embryo; and
(7) culturing the embryo obtained in step 6 to obtain a zebrafish notch1a mutant of stable inheritance.

In an embodiment, in step 2, the sequence of the target is show as GGAGTGTGTGAAAACCTGCG (SEQ ID NO. 1).

In an embodiment, in step 2, sequences of the primers for amplification are notch1aF shown as CGTGTGAGGTGGA-CATTA (SEQ ID NO. 4) and notch1aR shown as CATT-AGTTAAGTGAGGTGTGAG (SEQ ID NO. 5).

In an embodiment, in step 3, a sequence of the primer T7-notch1a-sfd is shown as TAATACGACTCACTATAG-GAGTGTGTGAAAACCTGCGGTTTTAGAGCTAGA AATAGC (SEQ ID NO. 2).

In an embodiment, in step 3, a sequence of the primer tracr rev is shown as AAAAAAAGCACCGACTCGGTGC-CAC (SEQ ID NO. 3).

In an embodiment, in step 4, a sequence of the gRNA is a fixed sequence of a T7 promoter+the target sequence+the pUC19-gRNA, which is prepared by PCR amplification where the T7-notch1a-sfd and the tracr rev are used as primer pairs, and a pMD19-gRNA scaffold plasmid is used as a template, and a Phusion® High-Fidelity PCR Master Mix with HF Buffer is used; electrophoresis and gel extraction.

In an embodiment, in step 5, the Cas9 mRNA is prepared by a method comprising:
(i) linearizing the pXT7-hCas9 plasmid and digesting the linearized pXT7-hCas9 plasmid with Xba 1 endonuclease;
(ii) purifying the digested product using a DNA Clean&Contentrator TM-5 purification kit;
(iii) transcribing the Cas9 mRNA in vitro using an mMESSAGE mMACHINE T7 ULTRA transcription kit; and
(iv) tailing the transcribed product and determining a concentration using Nanodrop 2000c followed by storage at −80° C. for use.

In an embodiment, step 6 further comprises: mixing the gRNA with the Cas9 mRNA to produce a mixture and microinjecting the mixture into the one-cell stage zebrafish embryo; wherein a final concentration of the gRNA is 100 ng/µL and a final concentration of the Cas9 mRNA is 400 ng/µL.

In an embodiment, step 7 further comprises:
(i) performing a notch1a knockout detection on the zebrafish introduced with the gRNA and the Cas9 mRNA to determine mutation efficiency of the target of notch1a in $F_0$ zebrafish;
(ii) outcrossing a notch1a-knockout $F_0$ adult zebrafish with a wild-type zebrafish to generate $F_1$ embryos and identifying a genotype of the $F_1$ embryo; wherein the $F_1$ embryo is identified to be an $F_1$ zebrafish notch1a mutant;
(iii) incrossing the same $F_1$ notch1a zebrafish mutants to obtain an $F_2$ notch1a zebrafish mutant; and
(iv) identifying a genotype of the $F_2$ notch1a zebrafish mutant; wherein a homozygous lethal phenomenon is observed in a homozygous $F_2$ notch1a-knockout zebrafish mutant and the heterozygous $F_7$ notch1a-knockout zebrafish mutant is the notch1a zebrafish mutant of stable inheritance.

In an embodiment, in step (i), sequences of primers used in the notch1a knockout detection are notch1aF shown as CGTGTGAGGTGGACATTA (SEQ ID NO. 4) and notch1aR shown as CATTAGTTAAGTGAGGTGTGAG (SEQ ID NO. 5).

Compared to the prior art, the invention has the following beneficial effects.
1. The invention first employs CRISPR/Cas9 technique and a specific targeting site to knock out the notch1a in zebrafish.
2. The notch1a mutation can be stably inherited and facilitate the further study of the function of notch1a.
3. The notch1a mutant has a phenotype of obvious disorders of somite and intersegmental blood vessel.

BRIEF DESCRIPTION OF THE DRAWINGS

FIGS. 1a-1c schematically show the detection of notch1a knockout in $F_0$ zebrafish. (a) shows a PCR product of notch1a in $F_0$ zebrafish embryo; (b) shows the identification results of T7E1 endonuclease digestion; and (c) shows the sequencing result of the PCR product.

DETAILED DESCRIPTION OF EMBODIMENTS

Figure 2:
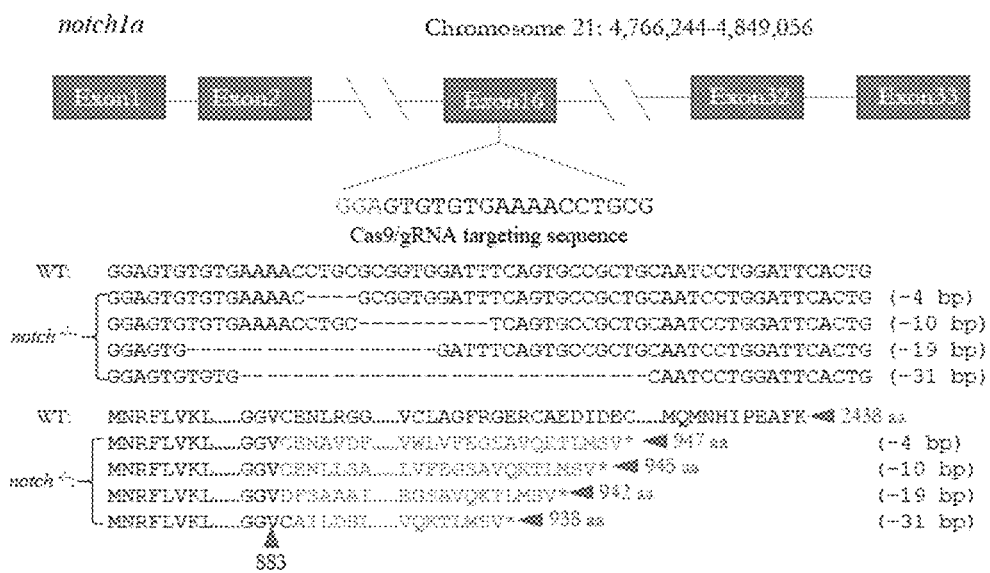
FIG. 2 shows the four notch1a mutation types in $F_1$ zebrafish.

The invention is further described with reference to the following embodiments. The following embodiments may help those skilled in the art to further understand the invention, but are not intended to limit the invention. It should be noted that various adjustments and improvements made by those skilled in the art without departing from the spirit of the invention should still fall within the scope of the invention.

EXAMPLE

1. Materials and Instruments 1.1 Zebrafish

The zebrafish used in this experiment were all AB strains and purchased from the Zebrafish Platform of Shanghai Institute of Biochemistry and Cell Biology, Chinese Academy of Sciences.

1.2 Plasmid pXT7-hCas9 plasmid and pUC19-gRNA scaffold plasmid were referred to a literature (Chang N, Sun C, Gao L, Zhu D, Xu X, Zhu X, Xiong J W, Xi J J. Genome editing with RNA-guided Cas9 nuclease in zebrafish embryos, Cell Res, 2013, 23 (4): 465-472).

1.3 Reagents

DNA Clean&Contentrator-5 (ZYMO RESEARCH, D4004); Ordinary DNA Purification Kit (TIANGEN BIOTECH CO., Ltd., DP204-03), MAXIscriptt® T7 in vitro Transcription Kit (Ambion, AM1314); Anhydrous Ethanol (Sinopharm Chemical Reagent Co., Ltd., 10009218); GenCrispr NLS-Cas9-NLS (GenScript, Z203389-25); Premix Taq™ (Ex Taq™ Version 2.0 plus dye) (TAKARA, RR902); DNA Marker I (TIANGEN BIOTECH CO., Ltd., MD101-02), T7 endonuclease 1 (NEW ENGLAND BioLab® Inc., M0302L); Rapid Plasmid Miniprep Kit (TIANGEN BIOTECH CO., Ltd., DP105); DH5α Competent Cells (TIANGEN BIOTECH CO., Ltd., CB101-03), LB Broth (Sangon Biotech (Shanghai) Co., Ltd., D915KA6602); LB Broth agar (Sangon Biotech (Shanghai) Co., Ltd., D911KA6566); and pMDTM19-T Vector Cloning Kit (TAKARA, 6013).

1.4 Instruments

PCR instrument (BIO-RAD, c1000 Touch™ Thermal Cycler); Centrifuge (Eppendorf, Centrifuge 5424); Vortex mixer (VORTEX-GENIE, G560E); Spectrophotometer (Thermo Scientific, Nanodrop 2000c); Electrophoresis instrument (BIO-RAD, PowerPac Basic); Gel imager (BIO-RAD, Gel Doc EZ Imager); Electronic balance (METTLER TOLEDO, AL104); Glass capillary (WPI, TW100F-4); Pure water system (Millipore, Milli-Q Direct 8); Vertical puller (NARISHIGE, PC-10); Thermostatic shaker (Innova, 40R), Microgrinder (NARISHIGE, EG-400), Micromanipulator (Warner Instruments. PL1-100A Plus); Thermostatic water bath (Shanghai Jing Hong Laboratory Instrument Co., Ltd., H1401438, DK-8D); 4° C. Refrigerator (Haier, HYC-610); −40° C. Low-temperature refrigerator (Haier, DW-40L508); −80° C. Ultra-low temperature freezer (Panasonic, MDF-U53V); and High-pressure Steam Sterilization Pot (SANYO Electric Co., Ltd., MLS-3780).

2 Method

2.1 Synthesis of gRNA (1) Design of target a. Searching of sequence

The Ensembl database was searched and the sequence of notch1a gene in the zebrafish was downloaded.

b. Design of target

The target was designed on the 16th exon sequence of the notch1a according to http://zifit.partners.org/ZiFiT/ChoiceMenu.aspx, and was shown in Table 1. The sequence of the target was shown in GGAGTGTGTGAAAACCTGCG (SEQ ID NO.1).

TABLE 1

Target site sequence of notch1α gene

| Gene | Chromosome | Gene length/ bp | mRNA length/ bp | Number of amino acids/aa | Number of introns | Number of exons | Target sequence (5'-3') | Exon |
|---|---|---|---|---|---|---|---|---|
| notch1α | 21 | 82812 | 7474 | 2438 | 32 | 33 | GGAGTGTGTGAAAACCTGCG | 16 | c. Detection for specificity of target

The designed target sequence was verified for the specificity by blast alignment on the NCBI website.

d. Detection of parents

The tail of the wild-type zebrafish used for gene knockout was cut for extraction of genomic DNA. Then the genomic DNA was used to amplify the target and the sequence near the target by PCR.

e. Detection of digestion

The sequence near the target in the wild-type zebrafish for gene knockout was detected by T7E1 endonuclease digestion.

f. Identification by sequencing

The PCR products were sequenced, and the obtained peak maps and sequences were aligned. The wild-type zebrafish having consistent sequence in this region were used as parents.

(2) Design of Primers for Detection

The primers were more than 100 by away from both sides of the target. Moreover, the difference, between the distance, from the upstream primer to the target and the distance from the downstream primer to the target was more than 100 bp. The amplified fragment had a length of about 500 bp (Table 2).

TABLE 2

Information about primers in the experiment

| Primer | Primer sequence (5'-3') | Fragment length/ bp | Length of the digested fragment/ bp |
|---|---|---|---|
| T7-notchα1-sfd | TAATACGACTCACTATAGGAGTGTGTGAAAACCTGCGGTTTTAGAGCTAGAAATAGC (SEQ ID NO. 2) | 120 | — |
| trac rev | AAAAAAAGCACCGACTCGGTGCCAC (SEQ ID NO. 3) | | — |
| notch1α-F | CGTGTGAGGTGGACATTA (SEQ ID NO. 4) | 213 | 144 + 99 |
| notch1α-R | CATTAGTTAAGTGAGGTGTGAG (SEQ ID NO. 5) | | |

(3) Synthesis of gRNA Product

The pUC19-gRNA scaffold plasmid was used as a template, and the fragment was amplified using primers T7-notch1a-sfd, tract rev and 2×EasyTaq PCR Super Mix (+dye), and purified using a kit.

(4) In Vitro Transcription

The reaction system was shown in Table 3.

TABLE 3

| Reaction system | |
|---|---|
| Nuclease-free Water | to 20 μL |
| DNA Template | 1 μg |
| 10 × Transcription Buffer | 2 μL |
| 10 mM ATP | 1 μL |

TABLE 3-continued

| Reaction system | |
|---|---|
| 10 mM CTP | 1 μL |
| 10 mM GTP | 1 μL |
| 10 mM UTP | 1 μL |
| T7 Enzyme Mix | 2 μL |

(It should be noted that 10 × Transcription Buffer and T7Enzyme Mix were finally added.)

The reaction system was mixed uniformly, centrifuged for a short time and incubated at 37° C. for 80 minutes. The reaction system was further added with 1 μL of TURBO DNase, mixed uniformly, centrifuged for a short time and incubated at 37° C. for 15 minutes.

(5) Purification of gRNA a. To the in vitro transcription system (20 μL) were added LiCl (2.5 μL, 4 M) and absolute ethanol (100 μL). The reaction system was mixed uniformly, centrifuged for a short time and stored in the −80° C. freezer for at least 1 hour.

b. Then the reaction system was transferred from the freezer and centrifuged at 4° C. and 12,000 rpm for 15 minutes. The supernatant was discarded, and the precipitate was washed with 70% ethanol and centrifuged at 4° C. and 8,000 rpm for 5 minutes. The supernatant was discarded and the centrifuge tube was transferred to a fume hood to allow the complete evaporation of the ethanol.

c. The gRNA precipitate was dissolved with 10 μL of DEPC water.

d. Concentration of the gRNA was measured using Nanodrop 2000 c.

2.2 Microinjection

The gRNA was mixed with the Cas9 mRNA and injected into the one-cell stage zebrafish embryos using a microinjector. A final concentration of the gRNA was 100 ng/μL and a final concentration of the Cas9 mRNA was 40 ng/μL.

2.3 Detection of Knockout Efficiency by T7E1 Digestion a. Extraction of embryo genome 5 embryos per group were added with NaOH (35 μL, 50 mM) and incubated at 95° C. for 20 minutes. During the incubation, the embryos were taken out and shaken. Then the embryos were added with Tris•HCl (3.5 μL, 1 M, pH≈8.0), shaken and centrifuged.

b. PCR amplification of the target fragment

The target fragment was amplified using, primers notch1a F (SEQ ID NO. 4) and notch1a R (SEQ ID NO. 5) presented in the table.

c. T7E1 endonuclease digestion detection

TABLE 4

| T7E1 digestion system | |
|---|---|
| $H_2O$ | to 10 μL |
| PCR product | 5 μL |
| Buffer | 1.1 μL |

The system was incubated at 95° C. for 5 minutes, cooled to room temperature, added with 0.25 μL of T7E1 enzyme and incubated at 37° C. for 45 minutes.

d. Electrophoretic detection and knockout efficiency detection

After electrophoresis, the agarose gel was imaged using a gel electrophoresis imager, and the knockout efficiency was calculated.

2.4 Detection of Phenotype of Homozygous $F_2$ Zebrafish notch1a Mutant

The $F_2$ zebrafish notch1a embryos were photographed and the number of embryos showing a phenotype was counted.

2.5 Phenotype Counting of Different Mutation Types

Counting of phenotypes and identification of genotype were performed on $F_2$ zebrafish embryos of different deletion types.

3 Experimental Results 3.1 Construction of notch1a Mutant 3.1.1 Results of notch1a Knockout Detection in $F_0$ Zebrafish The results showed that the notch1a gene was successfully knocked out, and the knockout efficiency calculated to be 40% or more by Image Lab 5.1 software. The sequencing peaks showed the presence of overlapping peaks at the 20 bp-length target site, demonstrating the successful knockout (FIGS. 1a-1c).

3.1.2 Detection of $F_1$ Zebrafish notch1a Mutant

Genotype detection of $F_1$ zebrafish demonstrated that there was a total of four mutation types, consisting of 4 bp deletion, 10 bp deletion, 19 bp deletion and 31 bp deletion in the vicinity of the target. The early termination will occur when the mutated sequences were used as templates for the encoding of amino acid (FIG. 2). The notch1a can encode 2438 amino acids, while the translation termination occurred at the amino acid residue 947 in the 4 bp-deletion mutant, at the amino acid residue 945 in the 10 bp-deletion mutant, at the amino acid residue 942 in the 19 bp-deletion mutant and at the amino acid residue 938 in the 31 bp-deletion mutant.

3.1.3 Detection of $F_2$ Zebrafish notch1a Mutant

Statistical analysis of $F_2$ zebrafish revealed that the notch1a mutation has homozygous lethality and the specific death time was 10-13 days post fertilization (dpf) (Table 5).

TABLE 5

| Statistics of notch1a mutation death | | | |
|---|---|---|---|
| Size | Total number | Number of deaths | Ratio |
| 10 dpf | 116 | 23 | 19.8% |
| 11 dpf | 116 | 33 | 28.4% |
| 12 dpf | 116 | 45 | 38.8% |
| 13 dpf | 116 | 15 | 13.0% |

3.1.4 Phenotypic Identification of $F_2$ notch1a Mutant

Figure 3:
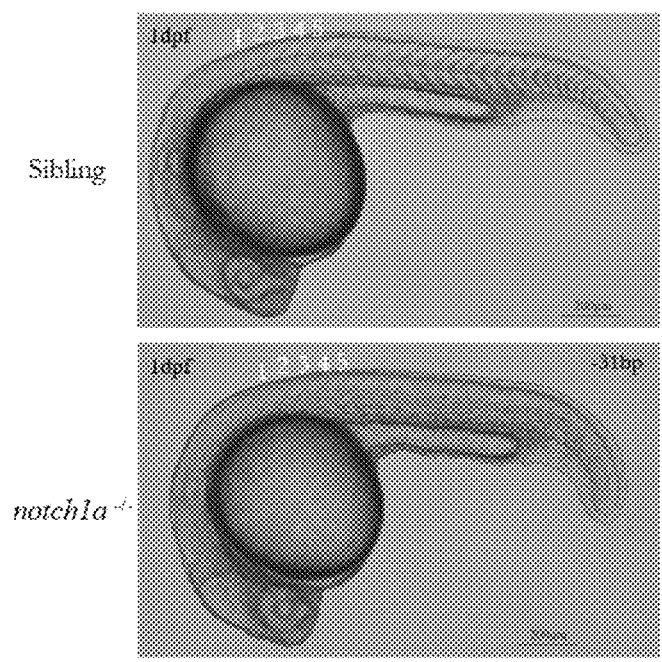
FIG. 3 shows the phenotypic identification of a homozygous $F_2$ notch1a mutant involving 31 bp deletion.
Figure 4:
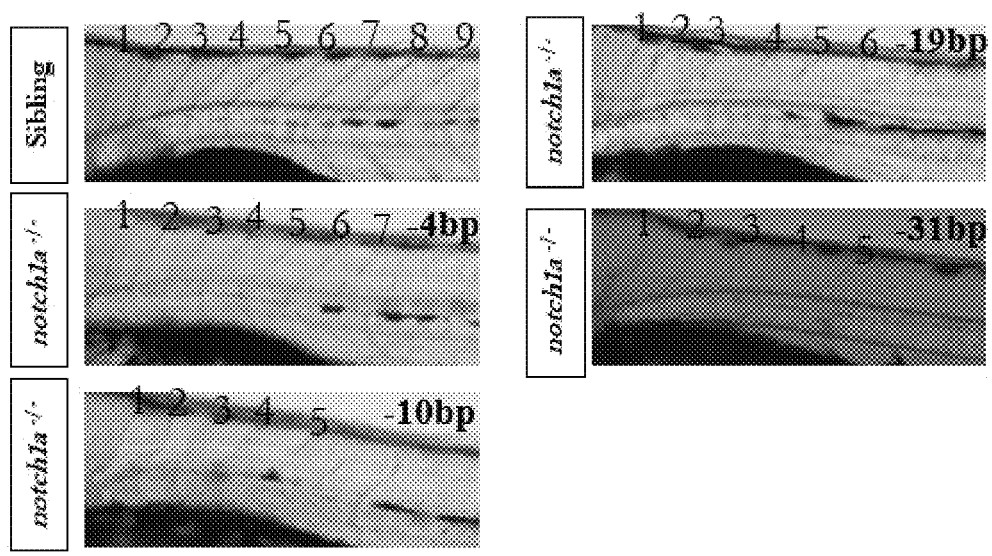
FIG. 4 shows the phenotypic identification of $F_2$ homozygous mutants of four different notch1a mutation types.
Figure 5:
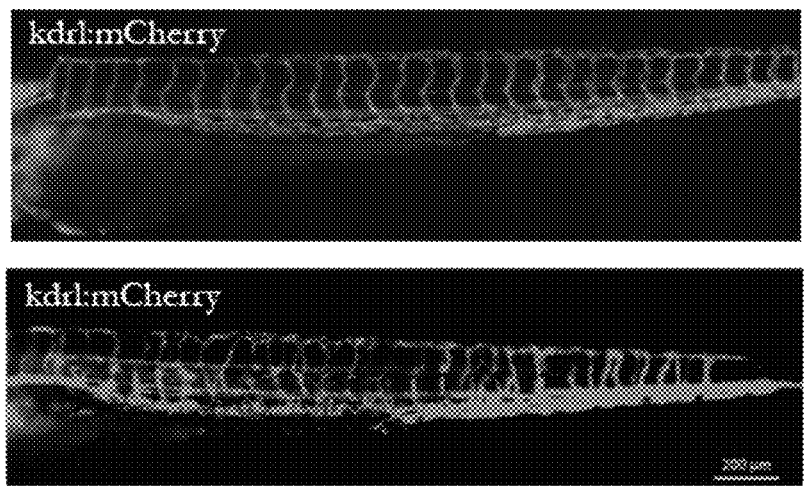
FIG. 5 shows the phenotype of somite and intersegmental blood vessel disorders in the notch1a mutant.

The phenotypic identification showed that a phenotype of somite boundary disorder may appear after the $5^{th}$-$7^{th}$ somite in the homozygous notch1a mutant (FIG. 3). Moreover, the identification for the homozygotes of different mutation types demonstrated that the four different mutation types of homozygotes showed a consistent phenotype (FIG. 4). In addition, the homozygous notch1a mutant also had a phenotype involving growth disorder of the intersegmental blood vessel (FIG. 5).

What is claimed is:

1. A method of making a genetically modified zebrafish comprising germ cells whose genomes' comprise a deletion in an endogenous notch1a gene, the method comprising:
   a) administering mRNA encoding Cas9 and guide RNA (gRNA) that targets the 16$^{th}$ exon of a zebrafish notch1a gene into a one-cell stage zebrafish embryo; and
   b) culturing the embryo obtained in step a) such that a genetically modified F$_0$ zebrafish comprising germ cells whose genomes' comprise a deletion in an endogenous notch1a gene is obtained;
   wherein the gRNA targets the nucleic acid sequence of SEQ ID NO: 1.

2. The method of claim 1, further comprising:
   c) crossing the zebrafish obtained in step b) to a wild-type zebrafish to obtain a genetically modified F$_1$ zebrafish whose genome comprises a heterozygous deletion in an endogenous notch1a gene; and optionally
   d) crossing F$_1$ zebrafish obtained in step c) to each other such that a genetically modified F$_2$ zebrafish whose genome comprises a homozygous deletion in an endogenous notch1a gene and capable of surviving for 10-13 days post fertilization is obtained.

3. The method of claim 1, wherein the gRNA is made by: i) determining a gRNA target sequence in the 16$^{th}$ exon of a zebrafish notch1a gene, ii) designing a primer consisting of the nucleic acid sequence of SEQ ID NO: 2 and a primer consisting of the nucleic acid sequence of SEQ ID NO: 3 for amplifying the gRNA target into a PCR product via PCR, and iii) transcribing the PCR product such that the gRNA that targets the 16$^{th}$ exon of a zebrafish notch1a gene is obtained.

4. The method of claim 1, wherein the mRNA encoding Cas9 is made by: i) linearizing plasmid pXT7-hCas9 using an Xba 1 endonuclease, ii) purifying the linearized plasmid, iii) transcribing the mRNA encoding Cas9 using the purified linearized plasmid, and iv) determining the concentration of the mRNA encoding Cas9.

5. The method of claim 1, further comprising mixing the mRNA encoding Cas9 and gRNA that targets the 16$^{th}$ exon of a zebrafish notch1a gene prior to administering into the one-cell stage zebrafish embryo.

6. The method of claim 1, wherein the administering mRNA encoding Cas9 and gRNA that targets the 16$^{th}$ exon of a zebrafish notch1a gene into a one-cell stage zebrafish embryo is via microinjection.

7. The method of claim 1, wherein a final concentration of the gRNA is 100 ng/μL and a final concentration of the mRNA encoding Cas9 is 400 ng/μL.

8. The method of claim 1, wherein step a) comprises: determining whether the zebrafish embryo comprises a deletion in an endogenous notch1a gene by using a primer consisting of the nucleic acid sequence of SEQ ID NO: 4 and a primer consisting of the nucleic acid sequence of SEQ ID NO: 5.

* * * * *